United States Patent
Shibata

(10) Patent No.: US 8,303,579 B2
(45) Date of Patent: Nov. 6, 2012

(54) SURGICAL OPERATION SYSTEM AND SURGICAL OPERATION METHOD

(75) Inventor: Norikiyo Shibata, Yamato (JP)

(73) Assignee: Olympus Medical Systems Corp., Tokyo (JP)

( * ) Notice: Subject to any disclaimer, the term of this patent is extended or adjusted under 35 U.S.C. 154(b) by 768 days.

(21) Appl. No.: 12/347,034

(22) Filed: Dec. 31, 2008

(65) Prior Publication Data
US 2010/0168742 A1    Jul. 1, 2010

(51) Int. Cl.
*A61B 18/04* (2006.01)
(52) U.S. Cl. .......... 606/27; 600/437; 600/439; 600/440; 600/442; 600/443; 600/444; 600/446; 600/455; 600/459; 600/468; 600/489; 601/2; 604/22; 606/1; 606/42; 607/2; 607/24; 607/3; 607/4; 607/50
(58) Field of Classification Search .......... 600/437, 600/439, 440, 442, 443, 444, 446, 455, 459, 600/468, 489; 601/2; 604/22; 607/2, 24, 607/3, 4, 50; 606/1, 27, 42
See application file for complete search history.

(56) References Cited

U.S. PATENT DOCUMENTS

| | | | | |
|---|---|---|---|---|
| 3,990,452 A | * | 11/1976 | Murry et al. ................. | 606/169 |
| 4,686,987 A | * | 8/1987 | Salo et al. .................. | 607/24 |
| 4,827,927 A | * | 5/1989 | Newton ....................... | 606/37 |
| 5,076,276 A | * | 12/1991 | Sakurai et al. ................ | 601/2 |
| 5,156,154 A | * | 10/1992 | Valenta et al. ............... | 600/455 |
| 5,190,517 A | * | 3/1993 | Zieve et al. .................. | 604/22 |
| 5,728,130 A | * | 3/1998 | Ishikawa et al. .............. | 606/185 |
| 5,883,309 A | * | 3/1999 | Vossiek et al. ................ | 73/602 |
| 5,931,836 A | | 8/1999 | Hatta et al. | |
| 6,306,131 B1 | * | 10/2001 | Hareyama et al. ............. | 606/38 |
| 6,360,611 B1 | * | 3/2002 | Toda ............................. | 73/651 |
| 6,454,781 B1 | | 9/2002 | Witt et al. | |
| 6,623,423 B2 | * | 9/2003 | Sakurai et al. ............... | 600/104 |
| 6,788,053 B2 | * | 9/2004 | Nekado et al. ............... | 324/256 |
| 6,860,852 B2 | * | 3/2005 | Schonenberger et al. .... | 600/439 |

(Continued)

FOREIGN PATENT DOCUMENTS

EP    1 820 460 A2    8/2007

(Continued)

OTHER PUBLICATIONS

International Search Report dated Feb. 23, 2010.

(Continued)

*Primary Examiner* — Nicholas Lucchesi
*Assistant Examiner* — Scott Medway
(74) *Attorney, Agent, or Firm* — Scully, Scott, Murphy & Presser, P.C.

(57) ABSTRACT

The surgical operation system includes a treatment section for treating a living tissue of a treatment target; an ultrasound generation section for providing ultrasound to the treatment section; an ultrasound drive power supply section for supplying ultrasound drive power to generate ultrasound to the ultrasound generation section; a high-frequency power supply section for supplying high-frequency power to the treatment section; an impedance detection section for detecting the impedance of the ultrasound provided to the living tissue and the impedance of the high-frequency power supplied to the living tissue; and a control section for controlling the ultrasound energy amount and the amount of high-frequency power or a crest factor value thereof in response to the detected impedance values of ultrasound and high-frequency wave.

24 Claims, 12 Drawing Sheets

U.S. PATENT DOCUMENTS

| | | | |
|---|---|---|---|
| 7,220,229 B2 * | 5/2007 | Lee et al. | 600/438 |
| 7,252,648 B2 * | 8/2007 | Honda et al. | 604/22 |
| 7,744,593 B2 * | 6/2010 | Mihori | 606/38 |
| 2002/0183774 A1 * | 12/2002 | Witt et al. | 606/169 |
| 2004/0082857 A1 * | 4/2004 | Schonenberger et al. | 600/439 |
| 2007/0191828 A1 | 8/2007 | Houser et al. | |
| 2008/0058803 A1 | 3/2008 | Kimura | |

FOREIGN PATENT DOCUMENTS

| | | |
|---|---|---|
| EP | 1 894 532 A1 | 3/2008 |
| JP | 8-299356 | 11/1996 |
| JP | 10-094545 | 4/1998 |
| JP | 10-225462 | 8/1998 |
| JP | 2000-271145 A | 10/2000 |
| JP | 2006-288431 | 10/2006 |
| JP | 2007-229454 | 9/2007 |
| JP | 2008-55151 | 3/2008 |
| WO | WO 97/34538 A1 | 9/1997 |

OTHER PUBLICATIONS

Supplementary European Search Report mailed Jun. 21, 2012 in corresponding European Patent Application No. 09836208.0.

* cited by examiner

SURGICAL OPERATION SYSTEM AND SURGICAL OPERATION METHOD

BACKGROUND OF THE INVENTION

1. Field of the Invention

The present invention relates to a surgical operation system and surgical operation method for performing a surgical operation with a treatment section by using ultrasound oscillation energy and high frequency electric energy.

2. Description of the Related Art

Recently in the field of surgery, there are widespread uses of an ultrasound drive apparatus which enables to perform a dissection treatment while coagulating a living tissue, an organ, or the like of an operation target by using ultrasound oscillation energy, and a high-frequency cauterization apparatus (a high-frequency power supply apparatus or an electric knife apparatus) for performing cauterization by applying high-frequency electric energy in a living tissue.

For example, in the electric surgical operation apparatus in a first prior art example according to Japanese Patent Application Laid-Open Publication No. 10-94545, ultrasound impedance is detected to monitor the hardness of a living tissue of a surgical target so that energy is supplied to an electric knife while the monitoring is performed. It also discloses that thereafter control is performed such that when the aforementioned ultrasound impedance becomes a predetermined value, the energy supply of the electric knife is stopped or changed.

Further, in the electric surgical operation apparatus in a second prior art example according to Japanese Patent Application Laid-Open Publication No. 10-225462, an impedance detection section for detecting the electrical impedance of a living tissue between a pair of electrodes is provided and a control section controls the energization/de-energization of high-frequency power based on the output signal of the impedance detection section.

The second prior art example discloses that the energization/de-energization of high-frequency power is controlled in accordance with an acoustic impedance of a living tissue associated with a cauterization procedure by high-frequency power.

Furthermore, in the ultrasound surgical operation apparatus of a third prior art example according to Japanese Patent Application Laid-Open Publication No. 2006-288431, it is disclosed that impedance detection means for detecting the electrical impedance of a living tissue is provided and amplitude control means is controlled in association with the detected electrical impedance.

Moreover, in recent years, there have been cases in which ultrasound oscillation energy and high-frequency electric energy are simultaneously supplied to a living tissue to perform coagulation dissection.

SUMMARY OF THE INVENTION

The surgical operation system of the present invention comprises:

a treatment section for treating a living tissue of a treatment target;

an ultrasound oscillation generation section for providing ultrasound oscillation to the treatment section;

an ultrasound drive power supply section for supplying ultrasound drive power to the ultrasound oscillation generation section;

a high-frequency power supply section for supplying high-frequency power to the treatment section;

an ultrasound impedance detection section for detecting the impedance of ultrasound provided to the living tissue via the treatment section;

a high-frequency impedance detection section for detecting the impedance of high-frequency power supplied to the living tissue via the treatment section;

a first control section for controlling an ultrasound energy amount generated by the ultrasound generation section in response to an ultrasound impedance value detected by the ultrasound impedance detection section; and a second control section for controlling high frequency energy generated by the high-frequency power supply section in response to a high-frequency impedance value detected by the high-frequency impedance detection section, The surgical operation method for performing a surgical operation on a living tissue of a treatment target using a treatment instrument according to the present invention, comprises:

a simultaneous supply step of simultaneously supplying ultrasound oscillation via an ultrasound oscillator and high-frequency power to a treatment section at a distal end of the treatment instrument;

an ultrasound impedance detection step of detecting an impedance of ultrasound oscillation applied to the living tissue via the treatment section;

a high-frequency impedance detection step of detecting an impedance of high-frequency power supplied to the living tissue via the treatment section;

a first control step of controlling an ultrasound energy amount generated by the ultrasound oscillator in response to an ultrasound impedance value detected by an ultrasound impedance detection step; and a second control step of controlling high frequency energy generated by the supplying of the high-frequency power in response to the high-frequency impedance value detected by the high-frequency impedance detection step.

DETAILED DESCRIPTION OF THE PREFERRED EMBODIMENTS

Hereinafter, the embodiments of the present invention will be described with reference to the drawings.
(First Embodiment)

A first embodiment of the present invention will be described with reference to FIGS. 1 to 8.

Figure 1:
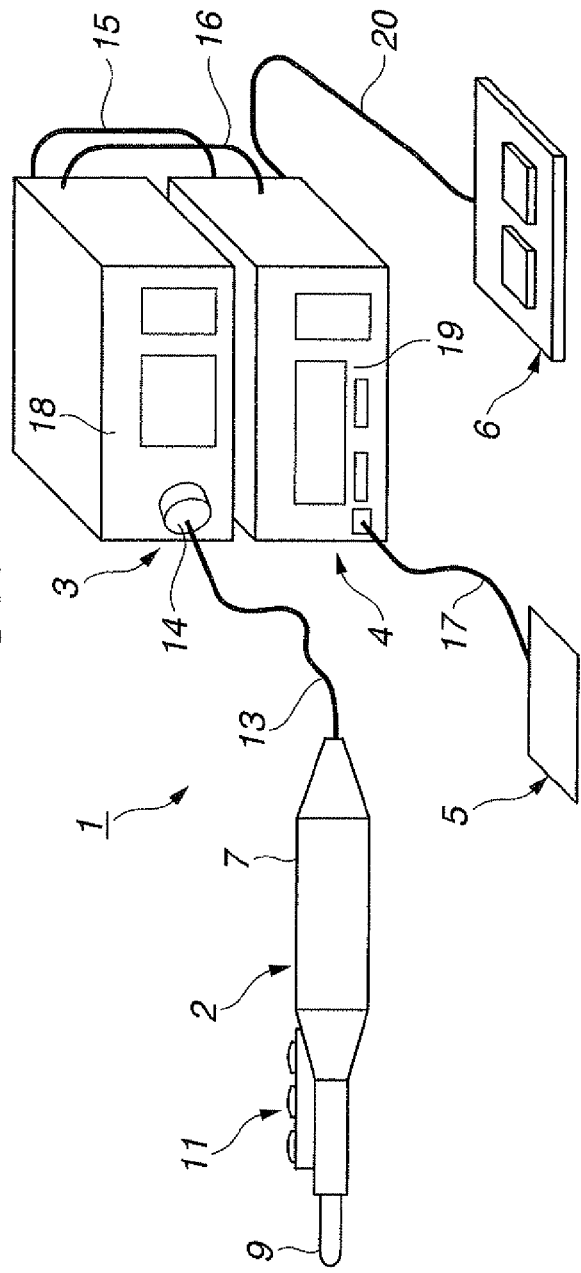
FIG. 1 is a perspective view to show an overall configuration of an ultrasound & high-frequency surgical operation system of a first embodiment of the present invention.

FIG. 1 shows an overall configuration of an ultrasound & high-frequency surgical operation system 1 of a first embodiment of the present invention. As shown in FIG. 1, the ultrasound & high-frequency surgical operation system 1 has a handpiece 2 as a surgical treatment instrument to perform a treatment such as coagulation dissection etc. by supplying an ultrasound oscillation energy and a high-frequency electric energy to a living tissue of a treatment target.

The ultrasound & high-frequency surgical operation system 1 has an ultrasound drive power supply apparatus (abbreviated as an ultrasound generator) 3 for supplying (outputting) an ultrasound drive power to generate ultrasound to an ultrasound transducer (or an ultrasound oscillator) 23 contained in the handpiece 2, and a high-frequency power supply apparatus (abbreviated as a high-frequency generator) 4 for supplying a high-frequency power (high-frequency current) to the handpiece 2.

The ultrasound & high-frequency surgical operation system 1 has a foot switch 6 for performing the instruction operation to turn on/off the supply of high-frequency power, and a counter electrode plate 5 for forming a return circuit of high-frequency power.

The handpiece 2 has a grasping section 7 to be grasped by an operator, and a probe 8 protruding forwardly from the grasping section 7; and there is provided a treatment section 9 for performing a treatment such as coagulation dissection at the distal end of the probe 8.

The grasping section 7 is provided with a handswitch unit (abbreviated as a handswitch) 11 for making selections when performing treatment with the treatment section 9. As the handswitch 11, there are provided a dissection selection switch 12a, a coagulation selection switch 12b, and further a simultaneous output switch 12c for simultaneously outputting ultrasound and high-frequency wave.

A signal cable 13 is configured to extend from the rear end side of the grasping section 7 of the handpiece 2, and the signal cable 13 is configured such that a connector 14 provided at its end is removably connected to a connector receptacle of the ultrasound generator 3.

Further, the ultrasound generator 3 and high-frequency generator 4 are connected with a communication cable 15 enabling signal transmission and reception. Moreover, the ultrasound generator 3 and the high-frequency generator 4 are connected with a high-frequency cable 16.

It is thus configured that a high-frequency wave generated by the high-frequency generator 4 is sent to the ultrasound generator 3 via the high-frequency cable 16 thereby supplying a high-frequency power (high-frequency current) to the handpiece 2 via the connector 14 and the signal cable 13.

There is removably connected to the high-frequency generator 4, an end section of a counter-electrode-plate cable 17 which is connected to the counter electrode plate 5. The counter electrode plate 5 is to be disposed to be in contact with the patient's hip or the like in a substantially large area.

Further, the ultrasound generator 3 and the high-frequency generator 4 are respectively provided with front panels 18 and 19 for performing various operations and displays, for example, in their front faces.

Furthermore, the foot switch 6 is connected with high-frequency generator 4 with a foot switch cable 20.

Figure 2:
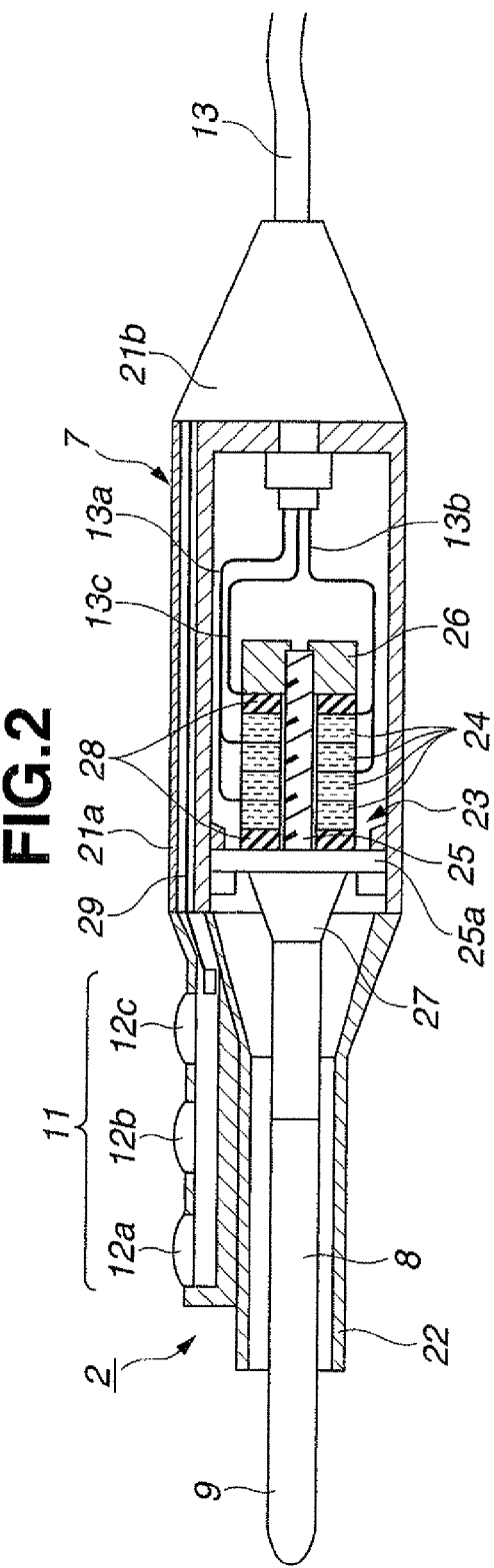
FIG. 2 is a sectional view to show the internal configuration of a handpiece.

FIG. 2 shows the internal structure of the handpiece 2. The handpiece 2 has a main case 21a, which has an approximately cylindrical shape and forms the grasping section 7, and to which front end a sheath 22 is connected. Further, the tail end side of the signal cable 13 is drawn into the main case 21a through its rear end section 21b. Also there is disposed in the main case 21a, an ultrasound transducer 23 as the ultrasound generation means to be connected to lead wires 13a and 13b for transferring ultrasound drive signal outputted from the ultrasound generator 3.

The ultrasound transducer 23 has a stacked structure formed of a plurality of ring-shape electrostrictive elements 24, and the plurality of electrostrictive elements 24 formed into a stacked structure are secured by being fastened by bolts 25 and nuts 26.

As the result of an ultrasound drive signal being applied to the electrode provided on each face of each electrostrictive element 24 through the lead wires 13a and 13b, the plurality of electrostrictive elements 24 oscillate at an ultrasound frequency.

The ultrasound oscillation (also referred to simply as ultrasound) is magnified by a horn 27 formed in a flange section 25a at the front end of the bolt 25 and is further transferred through the probe 8 to the treatment section 9 at its distal end.

That is, the treatment section 9 is provided with ultrasound oscillation via the ultrasound transducer 23 to which an ultrasound drive signal from the ultrasound generator 3 is applied. In other words, the ultrasound generator 3 and the ultrasound transducer 23 form an ultrasound supply section for providing ultrasound (oscillation) to the treatment section 9.

The operator can put the treatment section 9 oscillating at an ultrasound frequency on a treatment target portion to generate a friction heat by the ultrasound oscillation, and thus perform treatment such as coagulation dissection on the treatment target portion.

It is noted that an insulation plate 28 is disposed at each end of the plurality of electrostrictive elements 24.

A metal nut 26 forms a conductive section to which a lead wire 13c for high-frequency output in a signal cable 13 is connected. Then, when a high-frequency output signal is applied to the nut 26, the signal is transferred through a metal bolt 25 and a metal probe 8 to the treatment section 9 at the distal end thereof.

In this case, the operator can perform cauterization treatment by causing the treatment section 9 to come into contact with a treatment target portion so that a high-frequency current as a high-frequency electric energy flows in a high density through the contacted portion. Then, the high-frequency current returns to the high-frequency generator 4 through the counter electrode plate 5 and the counter electrode plate cable 17 which provide a return path.

Moreover, as shown in FIG. 2, the probe 8 is inserted into a metal sheath 22 covered with an insulation pipe not shown.

Further, a plurality of signal lines inserted into a handswitch cable 29 which is inserted in the signal cable 13 are connected to a dissection selection switch 12a, a coagulation selection switch 12b, and a simultaneous output switch 12c. Moreover, the dissection selection switch 12a, the coagulation selection switch 12b, and the simultaneous output switch 12c are covered with a rubber cover portion. Thus, it is possible to turn on/off each switch by pressing it over the rubber cover portion.

Figure 3:
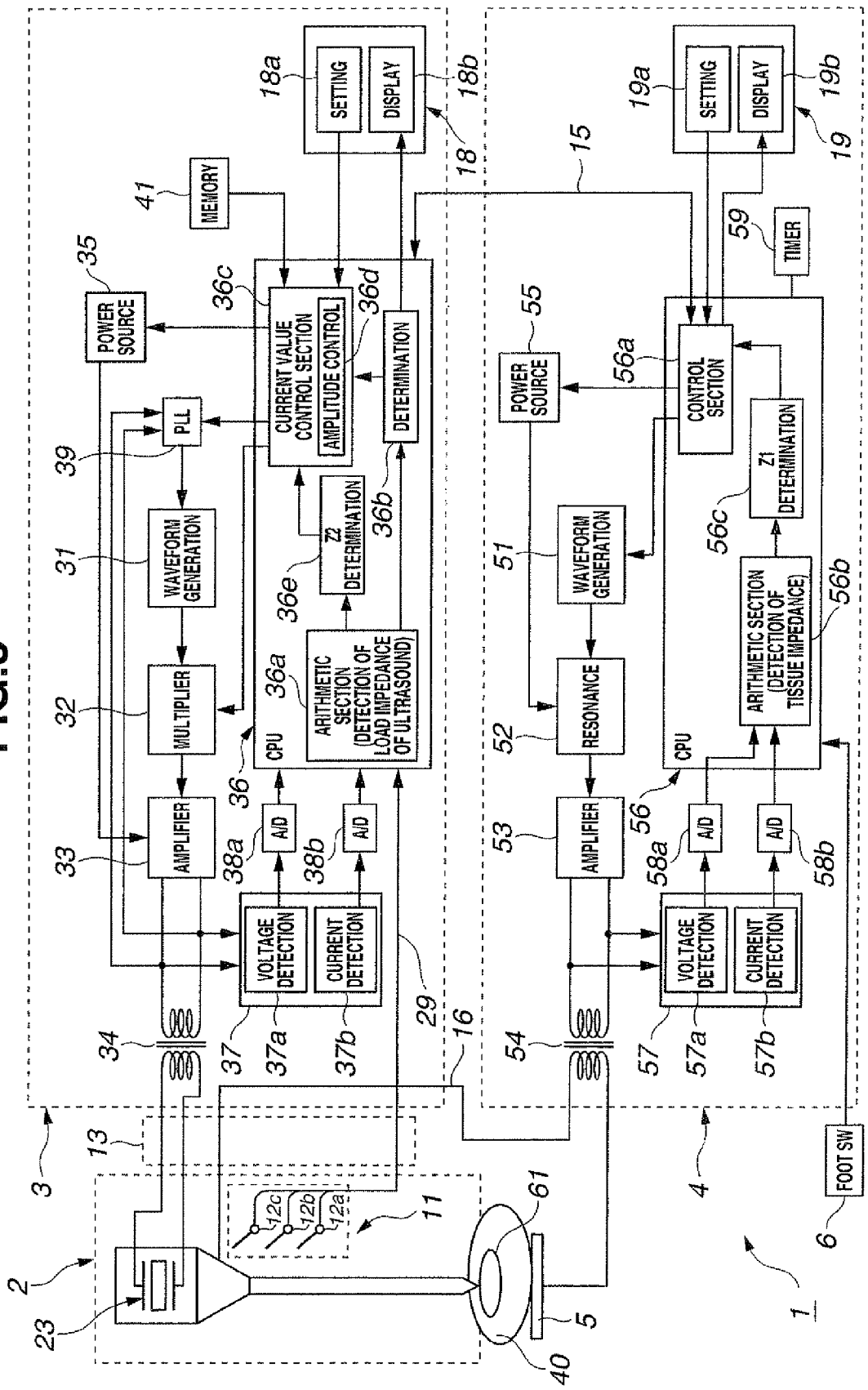
FIG. 3 is a block diagram to show a specific configuration of the ultrasound & high-frequency surgical operation system.

FIG. 3 shows a detailed configuration of the ultrasound generator 3 and the high-frequency generator 4 of FIG. 1. The ultrasound generator 3 incorporates a waveform generation circuit 31 for generating e.g. a sine wave signal.

A sine wave signal outputted from the waveform generation circuit 31 is subject to a constant current control by a multiplier 32, further amplified by an amplifier 33, and thereafter applied to the primary winding side of an output transformer 34. Then, the signal from the output terminal on the secondary winding side of the output transformer 34 is applied as an ultrasound drive signal to the ultrasound transducer 23 in the handpiece 2.

The amplitude of the ultrasound drive signal, that is, the amount of ultrasound output energy of the ultrasound transducer 23 is adjusted in response to the current value and the voltage value supplied to the amplifier 33 from a power source circuit 35. Thus, the ultrasound output is controlled by a central processing unit (CPU) 36 so as to be an appropriate current and voltage through a constant current control described below.

Moreover, the ultrasound drive signal outputted from the ultrasound generator 3 is converted into an ultrasound by the ultrasound transducer 23, so the energy amount of the ultrasound drive signal outputted from the ultrasound generator 3 and the energy amount of the ultrasound (oscillation) by the ultrasound transducer 23 are proportional to each other and are used interchangeably in the present embodiment.

The CPU 36 is inputted with a set value of ultrasound output by a setting section 18a of a front panel 18.

Further, the front panel 18 is provided with a display section 18b for displaying information such as an ultrasound output and the like outputted from the CPU 36.

A sine wave signal amplified by the amplifier 33 is inputted into a voltage detection circuit 37a and a current detection circuit 37b which constitute a detection section 37 so that a voltage and a current are detected (measured), respectively. Then, the detected voltage and current are each converted into digital values by A/D converters 38a and 38b and inputted into an arithmetic section 36a of the CPU 36. Further, the sine wave signal amplified at the amplifier 33 is inputted into a PLL circuit 39.

The PLL circuit 39 performs PLL control such that the ultrasound transducer 23 is driven by an ultrasound drive signal of a resonance frequency corresponding to the ultrasound transducer 23. Moreover, the control is performed such that the voltage and the current in the ultrasound drive signal are in phase. The operation of the PLL circuit 39 is controlled by the CPU 36.

The CPU 36 has a function of the arithmetic section 36a for performing arithmetic operations to calculate ultrasound output values using the voltage and current inputted via the A/D converters 38a and 38b.

Further the CPU 36 has a function of a determination section 36b for determining whether or not the ultrasound output value calculated by the arithmetic section 36a agrees with the set value by the setting section 18a. Then, the determination information is sent to a current value control section 36c by the CPU 36, and the current value control section 36c performs a constant current control based on the determination information such that the ultrasound output value agrees with the set value.

Furthermore, the current value control section 36c is connected with, for example, a memory 41, in which information such as the control value used for the immediately preceding control by the current value control section 36c is stored, and the current value control section 36c performs control with reference to the information such as an immediately preceding control value and the like stored in the memory 41.

For example, when being inputted with determination information indicating that the detected ultrasound output value is smaller than the set value, from the determination section 36b, the current value control section 36c refers to an immediately preceding control value thereby controlling the current to be larger than the control value.

When performing the current control, the current value control section 36c controls the multiplication value of a multiplier 32 in such a way to supplement the difference of the comparison result between an ultrasound output value and a set value.

Moreover, the arithmetic section 36a also has a function of detecting a mechanical impedance including the state of the load when the ultrasound transducer 23 is driven (specifically the state in which ultrasound oscillation energy is being applied from the treatment section 9 to a living tissue of a dissection treatment target), that is, a load impedance of ultrasound.

Further, the current value control section 36c also performs an amplitude control so as to hold the amplitude (or energy amount) of ultrasound at the treatment section 9 to be within a predetermined range (that is, a range suitable for the treatment of coagulation dissection). That is, the current value control section 36c also has a function of amplitude control 36d.

Performing the control to hold the amplitude of ultrasound oscillation at the position of the treatment section 9, with which actual treatment is performed, within a predetermined range, allows to prevent the sticking of the living tissue onto the treatment section 9 and to perform a smooth operation during the treatment of coagulation dissection.

It is noted that the frequency of ultrasound oscillation is 47 kHz in the present embodiment and, in this case, (the current value control section 36c of) the CPU 36 controls the amplitude of ultrasound oscillation to be not more than a set value with the lower limit being 50 μm as described below.

Further, the CPU 36 has a function of an impedance determination section 36e to determine whether or not the load impedance detected by the arithmetic section 36a is within a predetermined range (abbreviated as Z2 determination in FIG. 3).

Then, the current value control section 36c controls the amplitude (or current value) of ultrasound from the determination result by the impedance determination section 36e.

As shown in FIG. 3, an instruction operation signal by the switch operation of the dissection selection switch 12a, the coagulation selection switch 12b and the simultaneous output switch 12c is inputted to the CPU 36. Then, the CPU 36 performs the control corresponding to the instruction operation signal.

For example, when the operator turns the dissection selection switch 12a on, the CPU 36 sends the instruction operation signal to the CPU 56 of the high-frequency generator 4 through the communication cable 15, and causes a high-frequency output signal of a sine wave as a continuous wave for dissection to be outputted through the CPU 56.

When the operator turns on the coagulation selection switch 12b, the CPU 36 sends the instruction operation signal to the CPU 56 of the high-frequency generator 4 through the communication cable 15, and causes a coagulation wave of an intermittent waveform for coagulation, that is, a high-frequency output signal of a burst wave to be outputted through the CPU 56.

When the operator turns on the simultaneous output switch 12c, the CPU 36 controls the power source circuit 35 to turn on an ultrasound drive signal and to turn on a high-frequency output via the communication cable 15 through the CPU 56 of the high-frequency generator 4.

On the other hand, the high-frequency generator 4 incorporates a waveform generation circuit 51 for generating a sine wave and a burst wave, and the signal outputted from the waveform generation circuit 51 is inputted into an amplifier 53 through a resonance circuit 52.

The signal amplified by the amplifier 53 is applied to the primary winding side of the output transformer 54 and a high-frequency output signal for cauterization is generated on the secondary winding side.

One end of the secondary winding of the output transformer 54 is in conduction with a horn 27 etc. forming a conductor section in the handpiece 2. Moreover, the other end of the secondary winding is in conduction with a counter electrode plate 5 which is in contact with a patient 40 in a large area.

Further, the resonance circuit 52 is supplied with a power supply voltage from a variable voltage power source circuit 55, and the waveform generation circuit 51 and the power source circuit 55 are controlled by the CPU 56.

The operator can set a power set value of high-frequency etc. through the setting by a setting section 19a.

The control section 56a of the CPU 56 controls the waveform generation circuit S1 and the power source circuit 55 corresponding to the power set value etc. from the setting section 19a.

Further, the control section 56a of the CPU 56 causes a sine wave as a dissection wave to be outputted from the waveform generation circuit 51 when the dissection selection switch 12a is turned on by the operator.

The control section 56a causes a burst wave as a coagulation wave to be outputted from the waveform generation circuit 51 when the coagulation selection switch 12b is turned on.

Further, when the setting of an output mode for outputting a mixed wave is performed by the setting section 19a, the control section 56a causes a mixed wave (blended wave), in which a sine wave and a burst wave are mixed (blended), to be outputted.

Moreover, the control information etc by the control section 56a etc. of the CPU 56 is displayed on a display section 19b of a front panel 19.

The signal amplified by the above described amplifier 53 is inputted into a voltage detection circuit 57a and a current detection circuit 57b which constitute a detection section 57.

The voltage detection circuit 57a and the current detection circuit 57b detect (measure) the voltage and current of the signal amplified by an amplifier 53. The detected voltage and current are converted into a voltage and a current in digital form by A/D converters 58a and 58b and are inputted into the CPU 56.

The CPU 56 detects (calculates) a high-frequency impedance of a living tissue (also referred to as a tissue impedance) at an arithmetic section 56b using the inputted voltage and current. Then, the arithmetic section 56b outputs the detected tissue impedance value to an impedance determination section (abbreviated as Z1 determination in FIG. 3) 56c.

The impedance determination section 56c performs the determination of whether or not the inputted impedance value is within a predetermined impedance range by comparing the inputted impedance value with the threshold impedance value.

Then, the control section 56a performs the adjustment of high-frequency output according to the determination result of the impedance determination section 56c.

For example, when an impedance value is between a lower limit side threshold and an upper limit side threshold, the control section 56a maintains the output unchanged, and when the impedance value is smaller than the lower limit side threshold, the control section 56a adjusts the high-frequency output so as to reduce the high-frequency output. Moreover, when the impedance value is larger than the upper limit side threshold, the control section 56a adjusts the high-frequency output so as to increase the high-frequency output.

Further, after adjusting the high-frequency output according to the determination result of the impedance determination section 56c, the control section 56a further performs control such that the adjusted high-frequency output is not more than a set value.

Specifically, when the high-frequency output value is between ½ of the set value and the set value as describe below, the output value is maintained as it is, and when smaller than the ½ of the set value, the output is adjusted so as to be returned to ½ of the set value. Further, when the high-frequency output value is larger than the set value, the output is adjusted to be reduced to the set value.

Performing the control as described above makes it possible to keep an appropriate amount of high-frequency power for smoothly performing the treatment from the time of starting the treatment of coagulation dissection to a time at which the treatment has proceeded (to be describe below).

Further, the CPU 56 is also inputted with an ON/OFF signal from a foot switch 6. When the instruction operation of simultaneous output is performed by the foot switch 6, the CPU 56 provides an instruction to the CPU 36 to output an ultrasound drive signal thereby simultaneously outputting ultrasound and high-frequency wave.

Furthermore, a variant of the present embodiment has a function of performing control such that the output values of ultrasound and high-frequency wave are reduced from a set value of the initial state (that is, an initial set value) or otherwise limited after a predetermined set time has passed.

For that purpose, for example, the high-frequency generator 4 is provided with a timer 59 and when a set time period is set by a setting section 19a, the CPU 56 is set to be activated after the set time period by a timer 59.

Then the CPU 56 forcibly reduce the set value of high-frequency output at the initial setting after a set time period, and notifies the CPU 36 of the ultrasound generator 3 so that the CPU 36 forcibly reduces the set value of the ultrasound output at the initial setting.

In the present embodiment having such a configuration, the CPU 36 as the control means for the ultrasound generator 3 and the CPU 56 as the control means for the high-frequency generator 4 simultaneously perform the output start and the output termination of ultrasound and high-frequency wave via the communication cable 15.

Further, in a state in which ultrasound and high-frequency wave have been simultaneously outputted, the CPU 36 controls the ultrasound output by means of a current value in response to a detection result such as a load impedance detected at the ultrasound generator 3 side.

Furthermore, in a state in which ultrasound and high-frequency wave have been simultaneously outputted, the CPU 56 controls the high-frequency output in response to a detection result of the tissue impedance detected at the high-frequency generator 4 side.

Description will be made on the procedure of a surgical operation method of excising a living tissue 61 of a treatment target, such as an organ of a patient 40, in the ultrasound & high-frequency surgical operation system 1 having the above described configuration referring to FIG. 4.

The operator connects the handpiece 2 to the ultrasound generator 3 and the high-frequency generator 4 as shown in FIG. 1.

Then the power sources of the ultrasound generator 3 and the high-frequency generator 4 are turned on. Then, as shown in step S1, output setting is performed. For example, the operator performs the output setting of ultrasound and high-frequency wave. Further, it is supposed that the operator has selected for example a dissection mode as the output waveform mode of high-frequency wave.

As the outline is described in FIG. 3, the operator places the treatment section 9 at the distal end of the handpiece 2 at a treatment position for the living tissue 61 of a treatment target of excision. Then the operator turns on a simultaneous output switch 12c of the handswitch 11 as shown in step S2 in FIG. 4.

When the simultaneous output switch 12c is turned on, the instruction operation signal is transferred to the CPU 36 of the ultrasound generator 3, and further to the CPU 56 of the high-frequency generator 4 from the CPU 36.

Then, as shown in step S3, the CPU 56 causes the high-frequency output to start. Moreover, simultaneously, the CPU 36 of the ultrasound generator 3 causes the ultrasound output to start as shown in step S13.

As shown in step S3, the start of the high-frequency output causes a high-frequency wave to be supplied to the treatment section 9 side. Then, a high density high-frequency current flows to the living tissue 61 side of the treatment target in contact with the treatment section 9 and, at that moment, the living tissue 61 is dissected while being cauterized. Moreover, the high-frequency current flown to the living tissue 61 side is returned to the high-frequency generator 4 via the counter electrode plate 5.

In the next step S4, the arithmetic section 56b of the CPU 56 takes in digital values of the voltage measured by a voltage detection circuit 57a and the current measured by a current detection circuit 57b and starts the operation of detecting (measuring) the tissue impedance Z1 by dividing the voltage value by the current value.

The detected tissue impedance Z1 is inputted into an impedance determination section 56c, which determines whether or not it is within a predetermined impedance range (step S5). Specifically, determination is made on whether or not the tissue impedance Z1 is within an impedance range between 300 Ω and 500 Ω (300Ω<Z1<500 Ω). It is noted that 300 Ω is a lower limit side threshold and 500 Ω is a higher limit side threshold.

When it is determined by the impedance determination section 56c that the detected tissue impedance value Z1 is not less than 500 Ω, the control section 56a performs the control to increase the high-frequency output by a predetermined amount, for example, 5 W as shown in step S6, and thereafter the process returns to step S5.

Further, when it is determined by the impedance determination section 56c that the detected tissue impedance Z1 is not more than 300 Ω, the control section 56a performs the control to decrease the high-frequency output by a predetermined amount, for example, 5 W as shown in step S7, and thereafter the process returns to step S5.

When it is determined by the impedance determination section 56c that the detected tissue impedance Z1 is between 300 Ω and 500 Ω, the high-frequency output value is maintained and the process advances to step S8.

In step s8, the arithmetic section 56b starts the detection (measurement) of the output value of power given by the product of the voltage value and the current value measured by the voltage detection circuit 57a and the current detection circuit 57b respectively.

Then, the detected output value is inputted into the control section 56a, and the control section 56a performs the determination of whether or not the detected output value is within a range between the set value/2 and the set value in step S9.

When determining that the detected output value is not less than the set value, the control section 56a performs the control to decrease the output value to the set value (step S10), and the process returns to step S9.

When determining that the detected output value is not more than the set value/2, the control section 56a performs the control to increase the output value to the set value/2 (step S11), and the process returns to step S9.

When determining that the detected output value is within a range between the set value/2 and the set value, the control section 56a maintains the output value as shown step S12. Then the process proceeds to step S23.

On the other hand, when the ultrasound output is started as shown in step S13, ultrasound oscillation energy is supplied to the treatment section 9 so that the living tissue 61 of the treatment target is heated by the friction heat due to ultrasound oscillation and the living tissue is dissected while blood is being coagulated.

In next step S14, the arithmetic section 36a of the CPU 36 takes in digital values of the voltage measured by the voltage detection circuit 37a and the current measured by the current detection circuit 37b, and starts the detection (measurement) of mechanical impedance of the tissue, or a load impedance of ultrasound (hereinafter, referred to as a load impedance Z2) by dividing the voltage value by the current value.

The detected load impedance Z2 is inputted into an impedance determination section 36e, and the impedance determination section 36e performs the determination of whether or not it is within a predetermined impedance range shown in step S14. Specifically, it is determined whether or not the load impedance Z2 is within an impedance range between 200 Ω and 800 Ω (200Ω<Z2<800 Ω). It is noted that 200 Ω is a lower limit side threshold and 800 Ω is an upper limit side threshold.

When it is determined by the impedance determination section 36e that the detected load impedance Z2 is not less than 800 Ω, the current value control section 36c performs the control to increase the amplitude (current value) by a predetermined amount, specifically by about 10%, and thereafter the process returns to step S15. Further, when it is determined by the impedance determination section 36e that the detected load impedance Z2 is not more than 200 Ω, the current value control section 36c performs the control to decease the amplitude (current value) by a predetermined amount, specifically by about 10%, and thereafter the process returns to step S15.

When it is determined by the impedance determination section 36e that the detected load impedance Z2 is between 200 Ω and 800 Ω, the ultrasound output value is maintained, and thereafter the process proceeds to step S18.

In step S18, the arithmetic section 36a starts the detection (measurement) of the current value measured by the current detection circuit 37b.

Then the detected current value is inputted into (the amplitude control section 36d by the current value of) the current value control section 36c, and the current value control section 36c performs the determination of whether or not the detected current value is within a range between a current value corresponding to 50 μm and a set (current) value in step S19.

When determining that the detected current value is not less than the set value, the current value control section 36c performs the control to decrease the current value to the set value, and the process returns to step S19.

When determining that the detected current value is not more than the current value corresponding to 50 μm, the current value control section 36c performs the control to increase the current value to the current value corresponding to 50 μm, and the process returns to step S19.

Further, when determining that the detected current value is within a range between the current value corresponding to 50 μm and the set value, the current value control section 36c maintains the current value, that is, the output value as shown step S22. Then the process proceeds to step S23.

Through the processing in steps S18 to S22, the amplitude of the treatment section 9 is maintained within a predetermined range of amplitude value. Performing this control enables to reduce the sticking of the living tissue to the treatment section 9.

In step 23, the CPU 56 performs the determination of whether or not the simultaneous output switch 12c of the handswitch 11 is turned off and when it is not turned off, the process returns to steps S3 and S13 repeating the above described operations. On the other hand, when the simultaneous output switch 12c of the handswitch 11 is turned off, the CPUs 56 and 36 terminate the outputs of high-frequency wave and ultrasound. Thus, the processing of FIG. 4 is completed.

Figure 4:
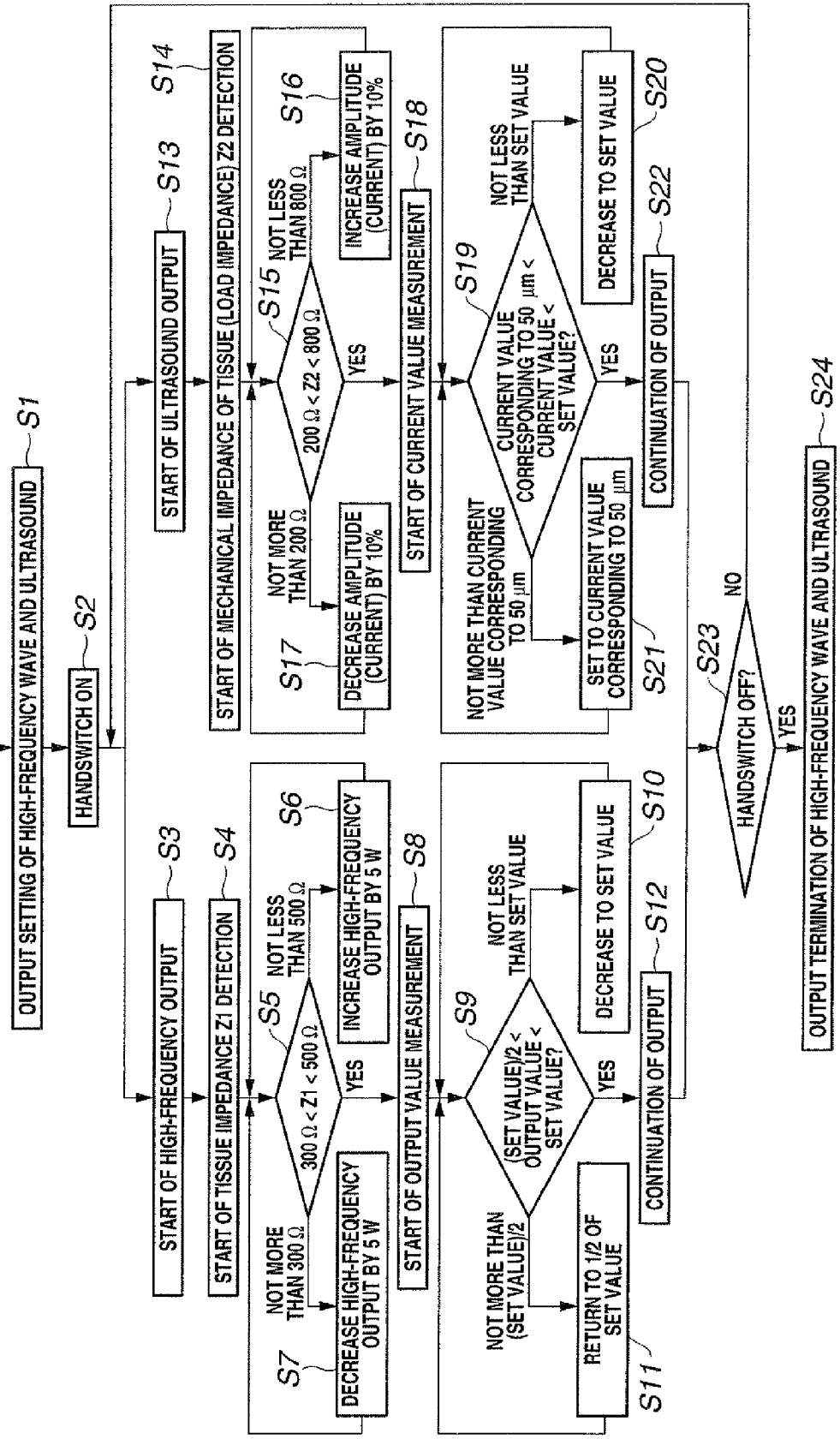
FIG. 4 is a flowchart to show the processing procedure of a surgical operation method relating to the first embodiment.
Figure 5:
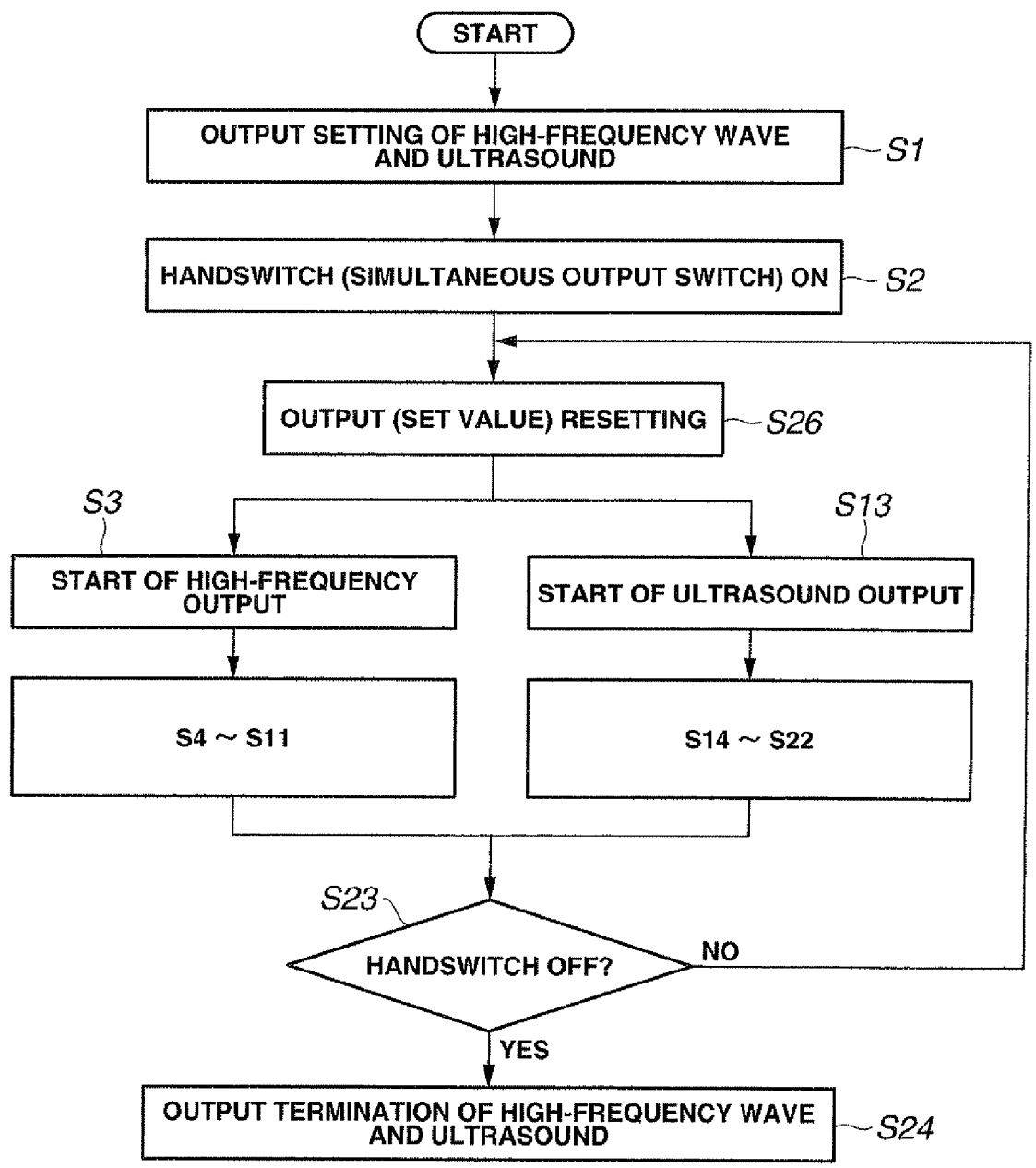
FIG. 5 is a flowchart to show another surgical operation method relating to the first embodiment.

In stead of the surgical operation method shown in FIG. 4, a variant of the surgical operation method shown in FIG. 5 may be adopted. In the surgical operation method shown in FIG. 5, the CPUs 56 and 36 perform the operation of output resetting of high-frequency wave and ultrasound after a set time period in step S26 between step S2 and steps S3 and S13 in the surgical operation method of FIG. 4.

Specifically, when a set time period preset by a timer 59 has elapsed, the CPUs 56 and 36 perform the resetting to forcibly decrease the set values of the high-frequency and ultrasound outputs, which have been set in step S1, to set values which are, for example, upper limit values of standard values. Other processings are the same as those of FIG. 4.

Figure 6:
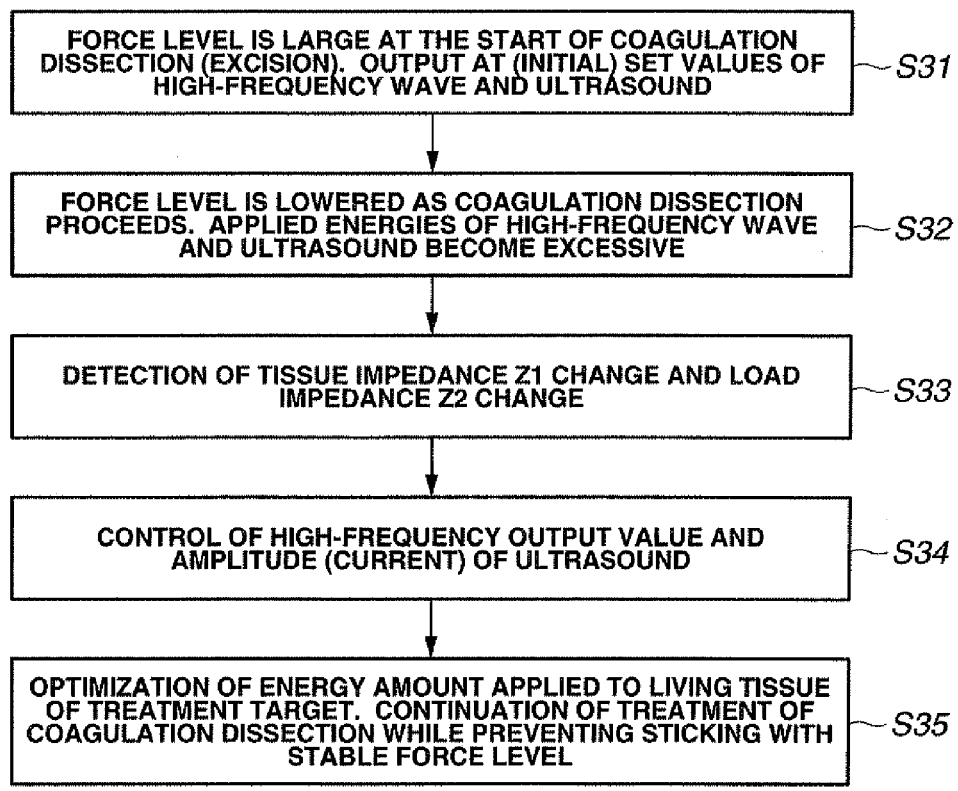
FIG. 6 is a flowchart to show the outline of a functional processing procedure in FIG. 4.
Figure 7A:
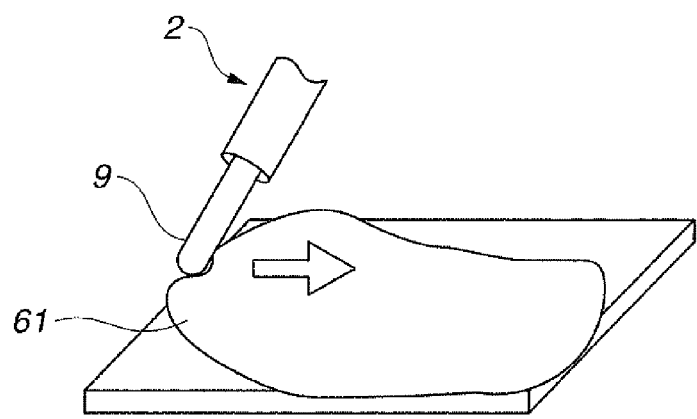
FIG. 7A shows the manner of treatment at the start of coagulation dissection.

The outline of the above described functional processings according to FIG. 4 is as shown in FIG. 6. As shown in step S31, at the start of coagulation dissection (excision), the force level which is required when the operator performs a coagulation dissection treatment is high. That is, as shown in FIG. 7A, at the start of coagulation dissection, the tissue impedance Z1 and the load impedance Z2 of a living tissue 61 of the treatment target are high, and therefore when the operator performs a coagulation dissection treatment by means of the handpiece 2, the force level required for the treatment becomes high.

For that reason, the high-frequency wave and ultrasound are outputted at (initial) set values as shown in step S31. In other words, the high-frequency and ultrasound treatments are performed at (larger) set values. In this case, since the force level for coagulation dissection is high, it is possible to smoothly perform coagulation dissection at the start of coagulation dissection.

Figure 7B:
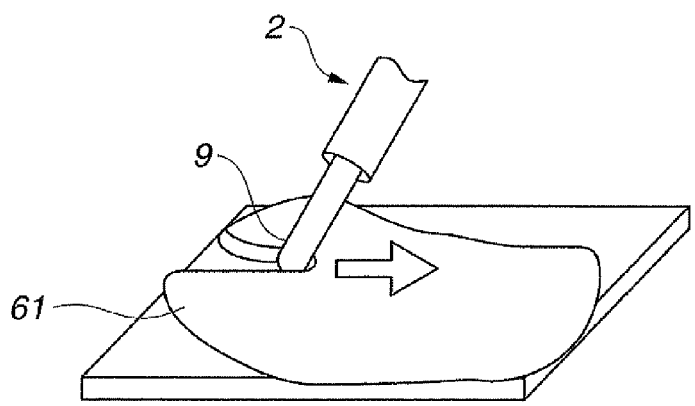
FIG. 7B shows a situation in which the treatment has proceeded from the start of coagulation dissection of FIG. 7A.

Thereafter, when the treatment of coagulation dissection has proceeded as shown in FIG. 7B, the tissue impedance Z1 and the load impedance Z2 of the living tissue 61 of the treatment target decrease. Therefore the force level required when the operator performs coagulation dissection with the handpiece 2 becomes lower.

That is, as the coagulation dissection proceeds as in step S32, the force level becomes lower. Therefore, if the set value in the case of step S31 remains the same, the amount of the high-frequency and ultrasound energies applied to the living tissue will become excessive.

To cope with the situation in which the amount of applied energy becomes excessive, the CPU 56 of the high-frequency generator 4 detects the change in the tissue impedance Z1 and the CPU 36 of the ultrasound generator 3 detects the change in the load impedance Z2 as shown in step S33.

In this case, the tissue impedance Z1 and the load impedance Z2 will decrease relative to the starting time.

Then, based on the detection results in step S33, the CPU 56 controls the high-frequency output value and the CPU 36 controls the amplitude (current value) of ultrasound as shown in step S34. Specifically, since the tissue impedance Z1 declines, the CPU 56 performs the control to reduce the high-frequency output value, and similarly since the load impedance Z2 declines, the CPU 36 performs the control to decrease the amplitude (current value) of ultrasound.

In this way, the high-frequency and ultrasound energies applied to the living tissue are optimized as shown in step S35. Thus, coagulation dissection is continued with a stable force level while preventing the sticking of the tissue.

Figure 8A:
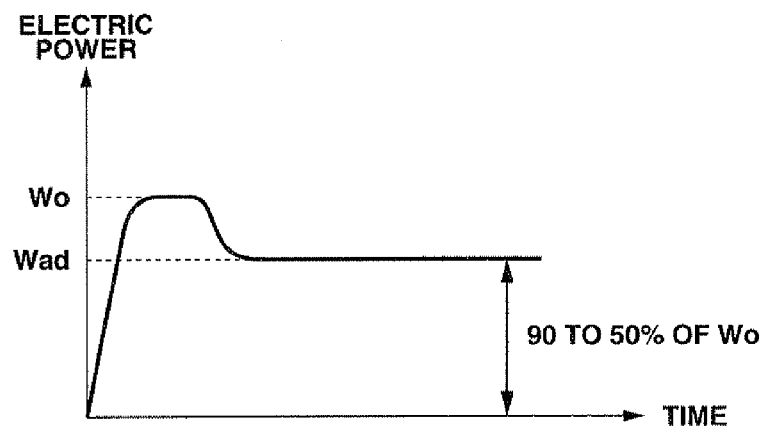
FIG. 8A shows an example of the temporal change of the high-frequency output value.

As the result of performing the above described treatment, the outline of the temporal change of the electric power (output) after the start of high-frequency output from the high-frequency generator 4 becomes as shown in FIG. 8A.

As shown in FIG. 8A, at the time of output start, an electric power value (set value) Wo set at the time of output start is outputted to perform treatment. As coagulation dissection proceeds, the tissue impedance Z1 declines and the electric power value is reduced in accordance with the decline. Then, with a reduced electric power value Wad (typically, 90 to 50% of the set value Wo), for example, a stable treatment is performed.

It is noted that as for the reduced electric power value Wad, if the initial set value by the operator is significantly deviated from a standard initial set value Wo, the set value/2 may be too large as the lower limit in the control loop of steps S9 to S11 in FIG. 4.

In this case, the initial set value can be adjusted to be a value closer to a standard set value Wo through the output resetting in step S26 of FIG. 5 so that the electric power changes in a characteristics as shown in FIG. 8A.

Figure 8B:
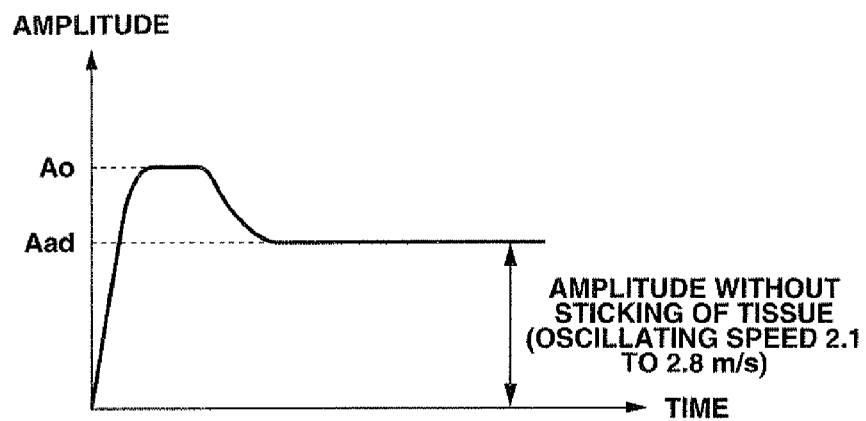
FIG. 8B shows an example of the temporal change of the amplitude of ultrasound output.

Similarly, the outline of the temporal change of the amplitude (current value) after the start of ultrasound output from the ultrasound generator 3 is as shown in FIG. 8B.

As shown in FIG. 8B, at the time of output start, treatment is performed at an amplitude Ao for the set value set at the time of output start. As coagulation dissection proceeds, the load impedance Z2 declines, and the amplitude is reduced in accordance with the decline. Then, with a reduced amplitude value Aad (2.1 m/s to 2.8 m/s when represented by an oscillating speed at the treatment section 9), for example, a stable treatment is performed.

When the amplitude of ultrasound is controlled to be within a predetermined range by the function of amplitude control 36d as described above, the value will change depending on the frequency and the like of the ultrasound.

For that reason, by using an oscillating speed which is given as the product of the amplitude and the frequency of an ultrasound and by setting the oscillating speed of the ultrasound at the treatment section 9 to be within the above described range, it is made possible to perform a stable treatment. In other words, instead of the amplitude control, the oscillating speed at the treatment section may be controlled.

By maintaining the above described amplitude value Aad, the operator can perform a stable coagulation dissection treatment without a sticking of the living tissue, with the treatment section 9.

In this case as well, when the initial set value by the operator is significantly deviated from a standard, normal set value, the set value may be too large as the upper limit value in the control loop of steps S19 to S21 in FIG. 4. In this case, the initial set value can be adjusted to be a value closer to a standard set value through the step of output resetting in FIG. 5 so that the amplitude changes in a characteristics as shown in FIG. 8B.

Thus, according to the present embodiment, when the living tissue 61 of a treatment target is subjected to coagulation dissection by use of handpiece 2 as the treatment instrument (surgical operation instrument), the treatment is performed at a set value when the treatment is started, and when the treatment has proceeded, the high-frequency power (output) or the ultrasound amplitude is automatically reduced to an appropriate level in accordance with the detected impedance, thereby allowing to smoothly perform a stable treatment.

Further the control method of high-frequency power or ultrasound amplitude according to the present embodiment will be simplified as the result of that although the high-frequency generator 4 and the ultrasound generator 3 communicate with each other, each generator is separately controlled in response to the detection result detected (measured) at respective generator side.

Further the method can ensure a better responsibility compared with a control method in which an impedance detected at one generator is sent to the other generator to perform control.

(Second Embodiment)

Next, a second embodiment of the present invention will be described with reference to FIGS. 9 to 13.

The appearance of the ultrasound & high-frequency surgical operation system 1 B of the present embodiment is the same as that of the ultrasound & high-frequency surgical operation system 1 shown in FIG. 1. Moreover, the structure of the handpiece 2 relating to the present embodiment is the same as that of the first embodiment.

Figure 9:
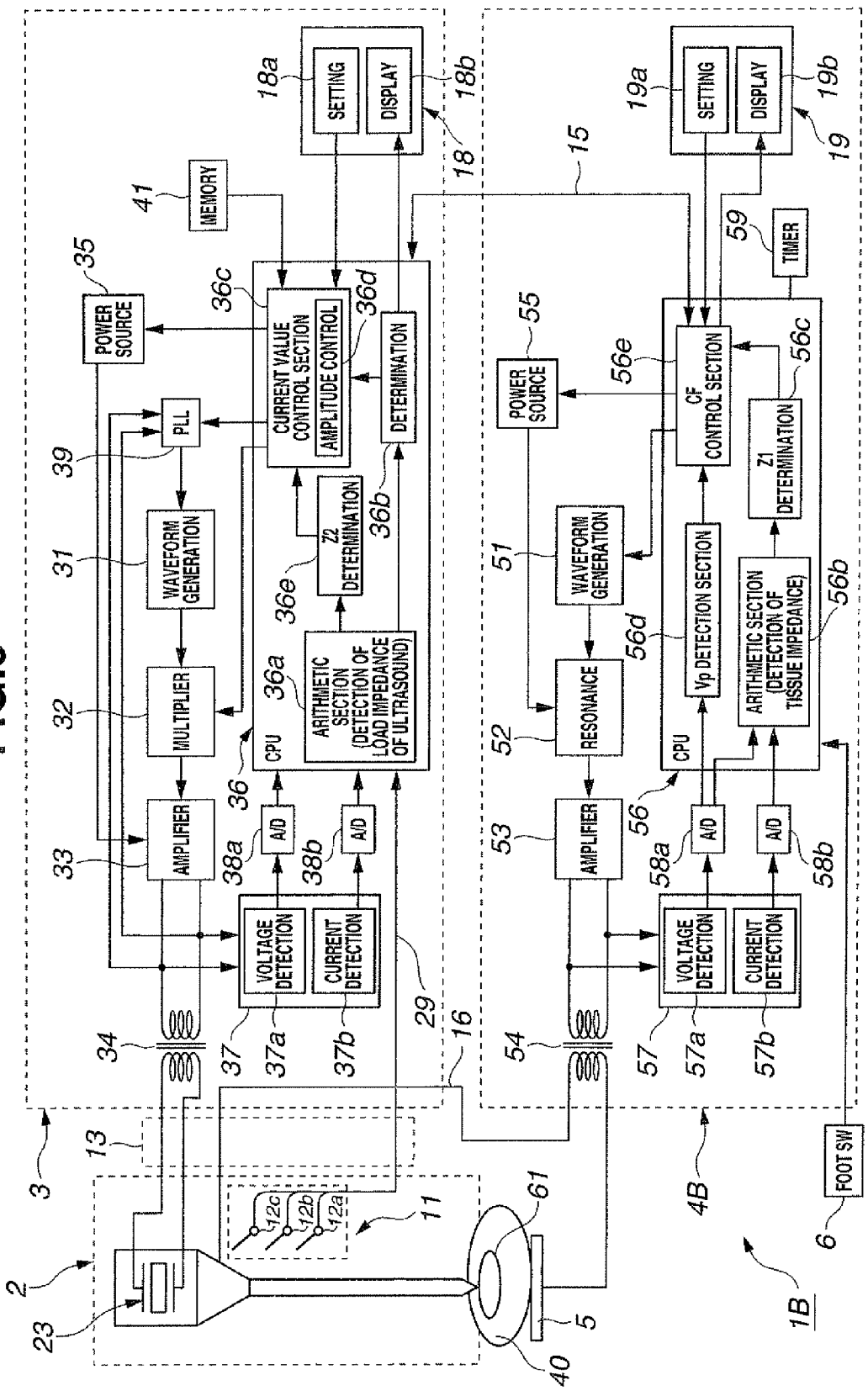
FIG. 9 is a block diagram to show the detailed configuration of the ultrasound & high-frequency surgical operation system of a second embodiment of the present invention.

FIG. 9 shows the configuration of the ultrasound & high-frequency surgical operation system 1B of the second embodiment of the present invention. The ultrasound & high-frequency surgical operation system 1B of the present embodiment utilizes a high-frequency generator 4B, in which a peak detection section (a Vp detection section in FIG. 9) 56*d* for detecting a peak value of voltage is provided in the CPU 56 and a CF control section 56*e* for performing the control to adjust the value of a crest factor (abbreviated as CF) are adopted in place of the control section 56*a* in the high-frequency generator 4 in the ultrasound & high-frequency surgical operation system 1 of FIG. 3.

Although in the first embodiment, description has been made on an example which utilizes a sine wave to provide a dissection wave as the high-frequency output signal, the present embodiment utilizes a mixed wave (a blended wave) which has an intermediate wave form and a property between a sine wave and a coagulation wave, and a burst wave as the coagulation wave.

Further, in the present embodiment, the CF of a mixed wave or a burst wave is adjusted in accordance with a detected tissue impedance Z1.

The peak detection section 56*d* outputs detected peak values to the CF control section 56*e*. In the case in which the CF control section 56*e* adjusts a CF value based on an inputted peak value, it also performs a peak value adjustment such that the peak value in that case is within a predetermined range.

Other configurations are the same as those of the first embodiment.

Figure 10A:
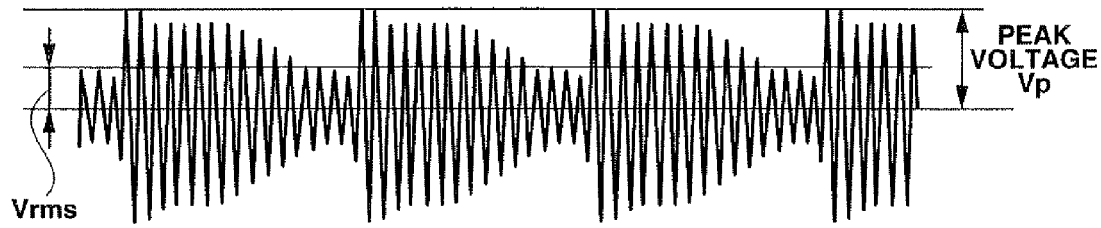
FIGS. 10A and 10B show a mixed wave and a burst wave.
Figure 10B:
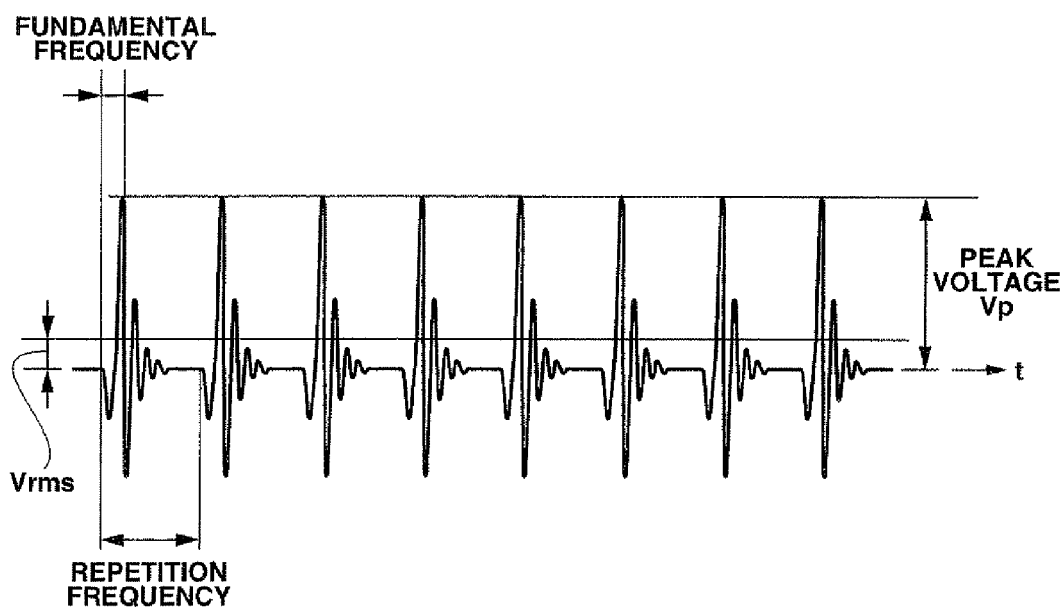

FIGS. 10A and 10B respectively show a mixed wave and a burst wave used in the present embodiment. A mixed wave shown in FIG. 10A has a damped waveform formed from a sine wave not shown, and the mixed wave has an intermediate waveform and a property between the sine wave and the burst wave of FIG. 10B.

While a sine wave has a continuous signal waveform of a fundamental wave of a fundamental frequency, a mixed wave and a burst wave have a period of repetition frequency (a repetition period) in which a plurality of signal waveforms of the fundamental frequency are repeated.

As shown in FIG. 10B, since a burst wave has a small number of fundamental waves having a large amplitude, its root-mean-square value of voltage (indicated as Vrms) is smaller with respect to its peak value of voltage (indicated as Vp). For this reason, a CF which is given as a peak value divided by a root-mean-square value becomes a larger value.

In contrast, the mixed wave shown in FIG. 10A has a larger root-mean-square value even when its peak value is smaller than that in the case of a burst wave since its fundamental wave has a certain value throughout its repetition period, and therefore has a smaller CF value compared with a burst wave.

Next, the surgical operation method of the present embodiment shown in FIG. 11 will be described. The surgical operation method shown in FIG. 11 has a processing configuration in which steps S6 and S7 and steps S10 and S11 in the surgical operation method of FIG. 4 are changed to steps S46 and S47 and steps S50 and S51 respectively.

As in the case of FIG. 4, the process starts with the setting of high-frequency and ultrasound outputs in step S1. However, in the present embodiment, the output mode of high-frequency will be described on the case in which a mixed wave is set to be outputted. An operation to turn on the handswitch 11 of step S2 causes the high-frequency output shown in step S3 and the ultrasound output of step S13 to start. In step S3, the high-frequency output starts in a mixed wave mode.

Then, in step S4, the detection of tissue impedance Z1 starts, and in next step S5, determination is made on whether or not the detected tissue impedance Z1 is within a rang between 300 Ω and 500 Ω.

When it is determined that the detected tissue impedance Z1 is not less than 500 Ω, the control section decrease the CF by a predetermined amount, for example, by 0.5 as shown in step S46, and thereafter the process returns to step S5.

On the other hand, when it is determined that the detected tissue impedance Z1 is not more than 300 Ω, the control section increases the CF by a predetermined amount, for example, 0.5 as shown in step S47 and thereafter the process returns to step S5.

When it is determined that the detected tissue impedance is within a range between 300 Ω and 500 Ω, the measurement of the output value of step S8 is started, and thereafter the process proceeds to step S9.

In step 89, the control section 56*a* determines whether or not the detected output value is within a range between the set value/2 and the set value.

When it is determined that the detected output value is not less than the set value, the control section 56*a* performs the control to increase the CF by a predetermined amount in step S50, and thereafter the process returns to S9.

When it is determined that the detected output value is not more than the set value/2, the control section 56a performs control to return the CF to a default value, and the process returns to step S9.

Further when it is determined that the detected output value is within a range between the set value/2 and the set value, the control section 56a maintains that output value as shown in step S12.

The rest is the same as FIG. 4.

Figure 11:
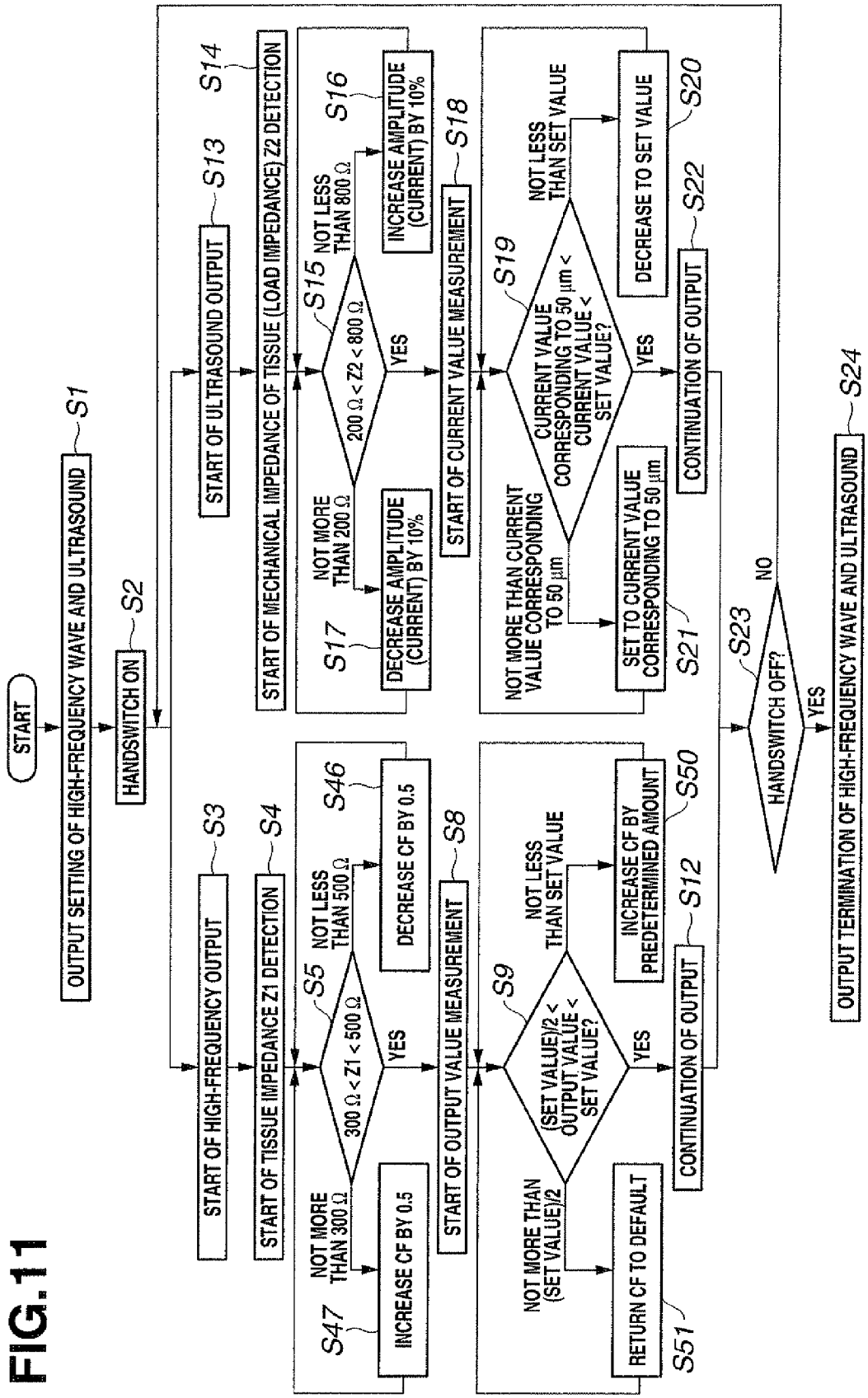
FIG. 11 is a flowchart to show the processing procedure of a surgical method relating to the second embodiment.
Figure 12:
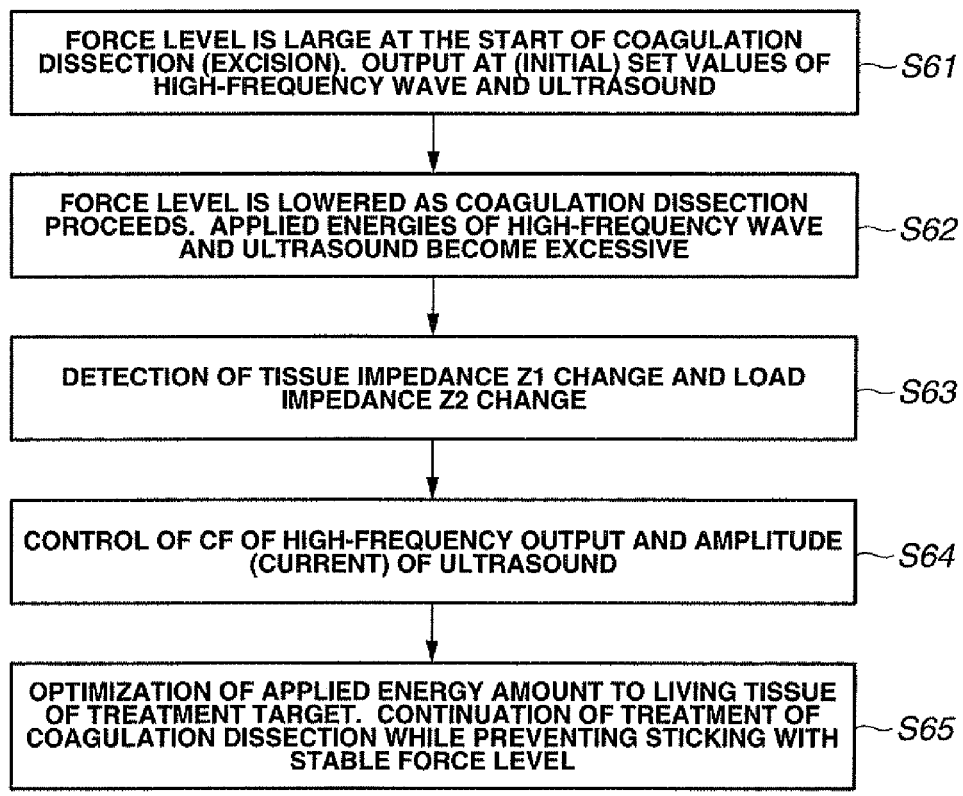
FIG. 12 is a flowchart to show the outline of a functional processing procedure in FIG. 11.

Next, the outline of functional processing for the processing of FIG. 11 is as shown in FIG. 12. As shown in step S61, the force level required for performing the operation of coagulation dissection (excision) is high at the start time of coagulation dissection. That is, as shown in FIG. 7A, at the start of coagulation dissection, the tissue impedance Z1 and load impedance Z2 of the living tissue 61 of a treatment target are high, and the force level when performing coagulation dissection is high.

For this reason, as shown in step S61, the high-frequency wave and ultrasound are outputted at (initial) set values. In other words, the treatments of high-frequency wave and ultrasound are performed at the set values.

Thereafter, as coagulation dissection proceeds as shown in FIG. 7B, the tissue impedance Z1 and load impedance Z2 of the living tissue 61 of a treatment target decline. Thereby, the force level when performing coagulation dissection becomes lower.

That is, as the coagulation dissection proceeds as shown in step S62, the force level becomes lower. For this reason, if the set value in the case of step S61 is kept unchanged, the amount of energies of high-frequency wave and ultrasound applied to the living tissue become excessive.

In correspondence to step S62, the CPU 56 of the high-frequency generator 4 detects the change of the tissue impedance Z1 and the CPU 36 of the ultrasound generator 3 detects changes of the load impedance Z2, as shown in step S63.

Then, based on the detection result of step S63, the CPU 56 controls the CF of the high-frequency output and the CPU 36 controls the amplitude (current value) of ultrasound as shown in step S64.

In this way, an optimization of the high-frequency and ultrasound energies applied to the living tissue is performed as shown in step S65. Then, coagulation dissection is continued while preventing sticking with a stable force level.

Figure 13:
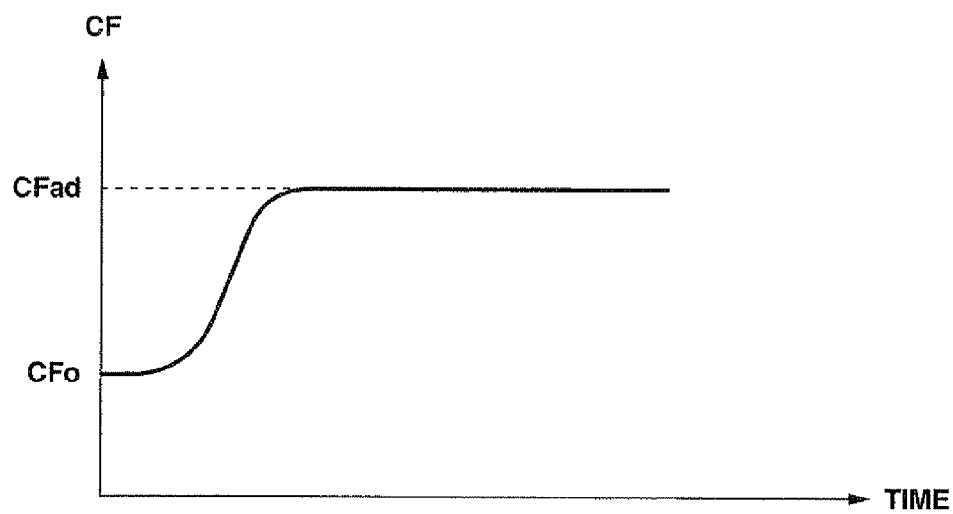
FIG. 13 shows an example of the temporal change of a crest factor of high-frequency output.

As the result of performing such treatment, the outline of temporal changes in CF after the start of high-frequency output from the high-frequency generator 4 becomes as shown in FIG. 13.

As shown in FIG. 13, at the time of output start, the treatment is performed at a CFo set at the time of output start, for example, 2 to 3 and at a root-mean-square value of 450 to 700 V. That is, at the time of output start, treatment is performed in a set condition in which dissection function with a lower CF value is given a priority.

Then, as coagulation dissection proceeds, the tissue impedance Z1 will decline and the CF value is increased in accordance with the decline. Then, a stable treatment is performed at an increased CF value CFad (for example, CFad is 3 to 6, and root-mean-square value is 270 to 550V).

Moreover, in the surgical operation method of FIG. 11, as described in the first embodiment, step S26 for performing output resetting may be added between step S2 and steps S3 and S13.

Further, in the case of a setting in which a mixed wave is outputted in the initial setting, the electric power value becomes lower than in the case of a sine wave. In other words, in the case of a mixed wave, it is unlikely to be set to be an excessively large value at the initial setting.

Figure 14:
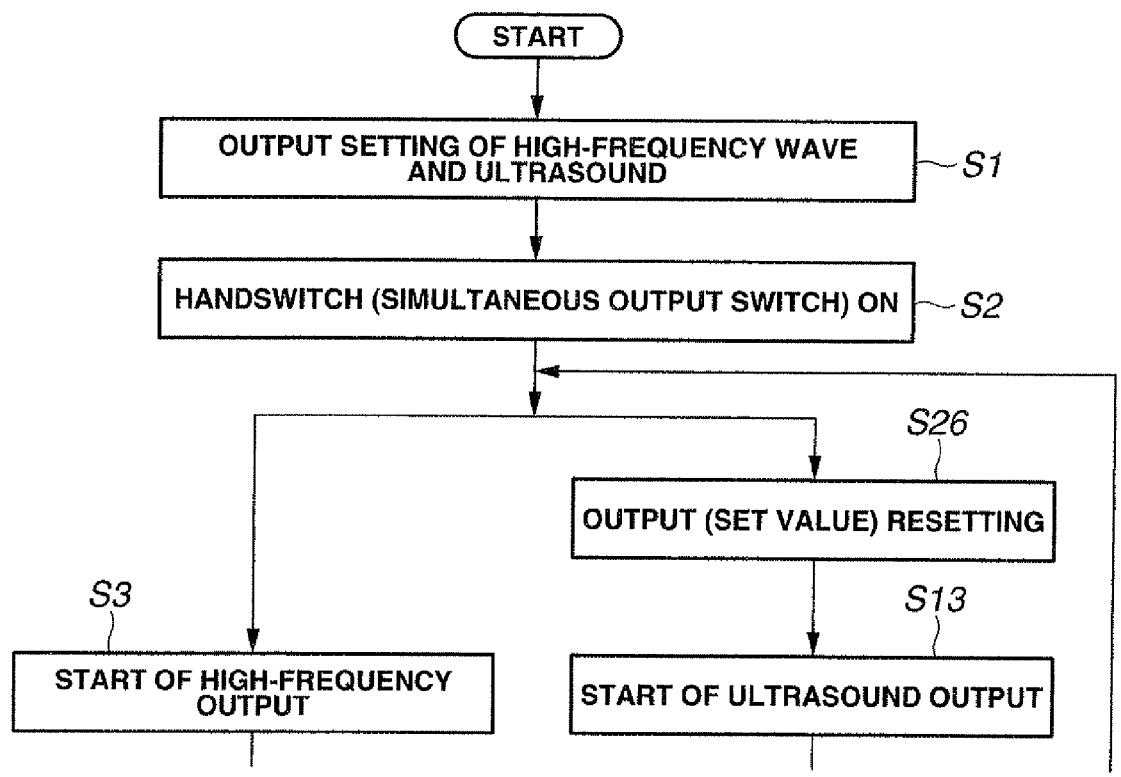
FIG. 14 is a flowchart to show a part of the processing procedure of another surgical operation method relating to the second embodiment.

For this reason, it may be configured as shown in FIG. 14 such that step S26 of performing output resetting is added to the ultrasound output side. In this case, it is possible to cope with a case in which the set value of ultrasound is set to be larger than a standard value.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgical operation system comprising:
a treatment section that treats a living tissue of a treatment target;
an ultrasound oscillation generation section that provides ultrasound oscillation, having an ultrasound energy amount required to treat the living tissue, to the treatment section;
an ultrasound drive power supply section that supplies drive power that generates the ultrasound oscillation to the ultrasound oscillation generation section;
a high-frequency power supply section that supplies high-frequency power, having a high-frequency energy amount required to treat the living tissue, to the treatment section;
an ultrasound impedance detection section that detects an ultrasound impedance value as a load impedance value when the ultrasound oscillation is provided to the living tissue via the treatment section;
a high-frequency impedance detection section that detects a high-frequency impedance value as a load impedance value when the high-frequency power is supplied to the living tissue via the treatment section;
a first control section that variably controls an increase and decrease of a value of the drive power that corresponds to the ultrasound energy amount generated by the ultrasound generation section in response to the ultrasound impedance value detected by the ultrasound impedance detection section in a state where the ultrasound oscillation and the high frequency power are supplied to the living tissue at the same time by the treatment section; and
a second control section that variably controls an increase and decrease of a value of the high-frequency power having the high frequency energy amount generated by the high-frequency power supply section in response to a high-frequency impedance value detected by the high-frequency impedance detection section in a state where the ultrasound oscillation and the high-frequency power are simultaneously supplied to the living tissue by the treatment section.

2. The surgical operation system according to claim 1, further comprising an oscillating speed control section that controls an oscillating speed of the ultrasound oscillation in the treatment section to be within a predetermined range.

3. The surgical operation system according to claim 1, further comprising a first determination section that determines whether or not the ultrasound impedance value detected by the ultrasound impedance detection section is within a range between a lower limit side threshold and a higher limit side threshold that are respectively preset as thresholds that determine whether or not to decrease and whether or not to increase the value of the drive power.

4. The surgical operation system according to claim 1, further comprising a second determination section that determines whether or not the high-frequency impedance value detected by the high-frequency impedance detection section is within a range between a lower limit side threshold and a higher limit side threshold that are respectively preset as thresholds that determines whether or not to decrease and whether or not to increase the value of the high-frequency power.

5. The surgical operation system according to claim 1, further comprising a third determination section that determines whether or not the ultrasound impedance value detected by the ultrasound impedance detection section is smaller than a lower limit side threshold that is preset as a threshold that determines whether or not to decrease the value of the drive power, wherein when it is determined by the third determination section that the ultrasound impedance value is smaller than the lower limit side threshold, the first control section performs control to decrease the value of the drive power by a predetermined amount.

6. The surgical operation system according to claim 1, further comprising a fourth determination section that determines whether or not the ultrasound impedance value detected by the ultrasound impedance detection section is larger than an upper limit side threshold that is preset as a threshold that determines whether or not to increase the value of the drive power, wherein when it is determined by the fourth determination section that the ultrasound impedance value is larger than the upper limit side threshold, the first control section performs control to increase the value of the drive power by a predetermined amount.

7. The surgical operation system according to claim 1, further comprising a fifth determination section that determines whether or not the high-frequency impedance value detected by the high-frequency impedance detection section is smaller than a lower limit side threshold that is preset as a threshold that determines whether or not to decrease the value of the high-frequency power, wherein when it is determined by the fifth determination section that the high-frequency impedance value is smaller than the lower limit side threshold, the second control section performs control to decrease the amount of high-frequency power which forms the high frequency energy.

8. The surgical operation system according to claim 1, further comprising a sixth determination section that determines whether or not the high-frequency impedance value detected by the high-frequency impedance detection section is smaller than a lower limit side threshold that is preset as a threshold that determines whether or not to decrease the value of the high-frequency power, wherein when it is determined by the sixth determination section that the high-frequency impedance value is smaller than the lower limit side threshold, the second control section performs control to increase the crest factor value of a high-frequency power waveform which forms the high frequency energy.

9. The surgical operation system according to claim 1, further comprising a seventh determination section that determines whether or not the high-frequency impedance value detected by the high-frequency impedance detection section is larger than an upper limit side threshold that is preset as a threshold that determines whether or not to increase the value of the high-frequency power, wherein when it is determined by the seventh determination section that the high-frequency impedance value is larger than the upper limit side threshold, the second control section performs control to increase the amount of high-frequency power which forms the high frequency energy.

10. The surgical operation system according to claim 1, further comprising an eighth determination section that determines whether or not the high-frequency impedance value detected by the high-frequency impedance detection section is larger than an upper limit side threshold that is preset as a threshold that determines whether or not to increase the value of the high-frequency power, wherein when it is determined by the eighth determination section that the high-frequency impedance value is larger than the upper limit side threshold, the second control section performs control to decrease the crest factor value of a high-frequency power waveform which forms the high frequency energy.

11. The surgical operation system according to claim 3, wherein when it is determined that the ultrasound impedance value detected by the ultrasound impedance detection section is within a range between a lower limit side threshold and a higher limit side threshold, it is further determined whether or not the ultrasound energy amount is within a predetermined range so that the ultrasound energy amount is controlled in response to the determination result.

12. The surgical operation system according to claim 4, wherein when it is determined that the high-frequency impedance value detected by the high-frequency impedance detection section is within a range between a lower limit side threshold and a higher limit side threshold, it is further determined whether or not the amount of the high-frequency power which forms the high frequency energy is within a predetermined range so that the amount of high-frequency power is controlled in response to the determination result.

13. The surgical operation system according to claim 1, further comprising a setting section, wherein after a predetermined time period from a starting time to provide ultrasound oscillation to the living tissue via the treatment section, the setting section sets the ultrasound energy amount to be provided to the living tissue by the ultrasound oscillation generation section to be lower than at the starting time.

14. The surgical operation system according to claim 1, further comprising a high-frequency power setting section, wherein after a predetermined time period from a starting time to supply high-frequency power to the living tissue via the treatment section, the high-frequency power setting section sets the amount of high-frequency power to be lower than the amount of high-frequency power at the starting time of supply.

15. The surgical operation system according to claim 1, wherein the ultrasound drive power supply section and the high-frequency power supply section simultaneously perform the operations of turning on/off the ultrasound drive power supply and turning on/off the high-frequency power supply by an on/off operation of a switch.

16. The surgical operation system according to claim 2, wherein the oscillating speed control section controls the oscillating speed to be within a predetermined range of 2.1 to 2.8 m/s.

17. The surgical operation system according to claim 4, wherein when it is determined that the high-frequency impedance value detected by the high-frequency impedance detection section is within a range between a lower limit side threshold and an upper limit side threshold, the second control section further performs the control to maintain the amount of high-frequency power which forms the high frequency energy to be within a range of 50 to 90% of the amount of high-frequency power at the time of initial setting.

18. A surgical operation method that performs a surgical operation on a living tissue of a treatment target using a treatment instrument, comprising:
- a simultaneous supply step of simultaneously supplying ultrasound oscillation having an ultrasound energy amount required to treat the living tissue via an ultrasound oscillator and high-frequency power having a high-frequency energy amount required to treat the living tissue to a treatment section at a distal end of the treatment instrument;
- an ultrasound impedance detection step of detecting an ultrasound impedance value in a state where the ultrasound oscillation is provided to the living tissue via the treatment section;
- a high-frequency impedance detection step of detecting a high-frequency impedance value in a state where the ultrasound oscillation is supplied to the living tissue via the treatment section;
- a first control step of variably controlling an increase and decrease of the ultrasound energy amount generated by the ultrasound oscillator in response to the ultrasound impedance value detected by an ultrasound impedance detection step in a state where the ultrasound oscillation and the high-frequency power are simultaneously supplied to the living tissue by the treatment section; and
- a second control step of variably controlling increase and decrease of a value of the high-frequency power in response to the high-frequency impedance value detected by the high-frequency impedance detection step in a state where the ultrasound oscillation and the high-frequency power are simultaneously supplied to the living tissue by the treatment section.

19. The surgical operation method according to claim 18, further comprising an oscillation speed control step of controlling the oscillating speed of the ultrasound oscillation in the treatment section to be within a predetermined range.

20. The surgical operation method according to claim 18, wherein when it is determined that the ultrasound impedance value detected by the ultrasound impedance detection step is within a range between a lower limit side threshold and a higher limit side threshold, the thresholds being preset that determines whether or not to decrease and whether or not to increase a value of the ultrasound energy amount, it is further determined whether or not the ultrasound energy amount is within a predetermined range so that the ultrasound energy amount is controlled in response to the determination result.

21. The surgical operation method according to claim 18, wherein when it is determined that the high-frequency impedance value detected by the high-frequency impedance detection step is within a range between a lower limit side threshold and a higher limit side threshold, the thresholds being preset that determines whether or not to decrease and whether or not to increase a value of the ultrasound energy amount, it is further determined whether or not the amount of high-frequency power which forms the high frequency energy is within a predetermined range so that the amount of high-frequency power or the crest factor value which forms the high frequency energy is controlled in response to the determination result.

22. The surgical operation method according to claim 4, further comprising a communication cable that connects the first control section with the second control section, wherein the communication cable sends control information from one of the first control section and the second control section to the other of the first control section and the second control section.

23. The surgical operation system according to claim 1, further comprising a setting section, wherein after a predetermined time period from a starting time to provide ultrasound oscillation to the living tissue via the treatment section, the setting section automatically sets the ultrasound energy upper limit side threshold to be provided to the living tissue by the ultrasound oscillation generation section to be lower than at the starting time; and
- a high-frequency power setting section, wherein after a predetermined time period from a starting time to supply high-frequency power to the living tissue via the treatment section, the high-frequency power setting section automatically sets the upper limit side threshold of high-frequency power to be lower than the upper limit side threshold of high-frequency power at the starting time of supply.

24. The surgical operation method according to claim 18, further comprising a first setting step of automatically setting an ultrasound energy upper limit side threshold to be provided to the living tissue by the ultrasound oscillation generation section to be lower than at the starting time after a predetermined time period from a starting time; and
- a second setting step of automatically setting an upper limit side threshold of high-frequency power to be lower than an upper limit side threshold of high frequency power at the starting time after a predetermined time period from a starting time of supply of the high frequency power to the living tissue.

* * * * *